United States Patent [19]

Rydell et al.

[11] Patent Number: 4,844,092
[45] Date of Patent: Jul. 4, 1989

[54] CATHETER Y-CONNECTOR WITH GUIDEWIRE LOCKING MEANS

[75] Inventors: Mark A. Rydell, Golden Valley; Richard L. Goodin, Blaine, both of Minn.

[73] Assignee: Schneider-Shiley (USA) Inc., Minneapolis, Minn.

[21] Appl. No.: 174,507

[22] Filed: Mar. 28, 1988

[51] Int. Cl.$^4$ .............................. A61M 25/00
[52] U.S. Cl. ...................... 128/772; 128/657; 604/164; 604/170
[58] Field of Search .......... 128/772, 656–658, 128/344; 604/93, 96, 103, 158, 164–165, 178, 170

[56] References Cited

U.S. PATENT DOCUMENTS

| | | | |
|---|---|---|---|
| 4,616,648 | 10/1986 | Simpson | 128/344 X |
| 4,619,263 | 10/1986 | Frisbie et al. | 128/344 |
| 4,638,805 | 1/1987 | Powell | 128/344 |
| 4,646,742 | 3/1987 | Packard et al. | 128/344 |
| 4,730,616 | 3/1988 | Frisbie et al. | 604/164 X |
| 4,748,982 | 6/1988 | Horzewski et al. | 128/344 |
| 4,753,238 | 6/1988 | Gaiser | 128/344 |

OTHER PUBLICATIONS

Buchbinder; WO 8 801885; 3-1988.

Primary Examiner—Kyle L. Howell
Assistant Examiner—Angela D. Sykes
Attorney, Agent, or Firm—Orrin M. Haugen; Thomas J. Nikolai; Frederick W. Niebuhr

[57] ABSTRACT

A Y-connector for attachment to the proximal end of a guide catheter which includes an arm projecting from the side of the Y-connector, the arm including a clamp for securing a catheter guidewire against movement relative to the guide catheter.

9 Claims, 1 Drawing Sheet

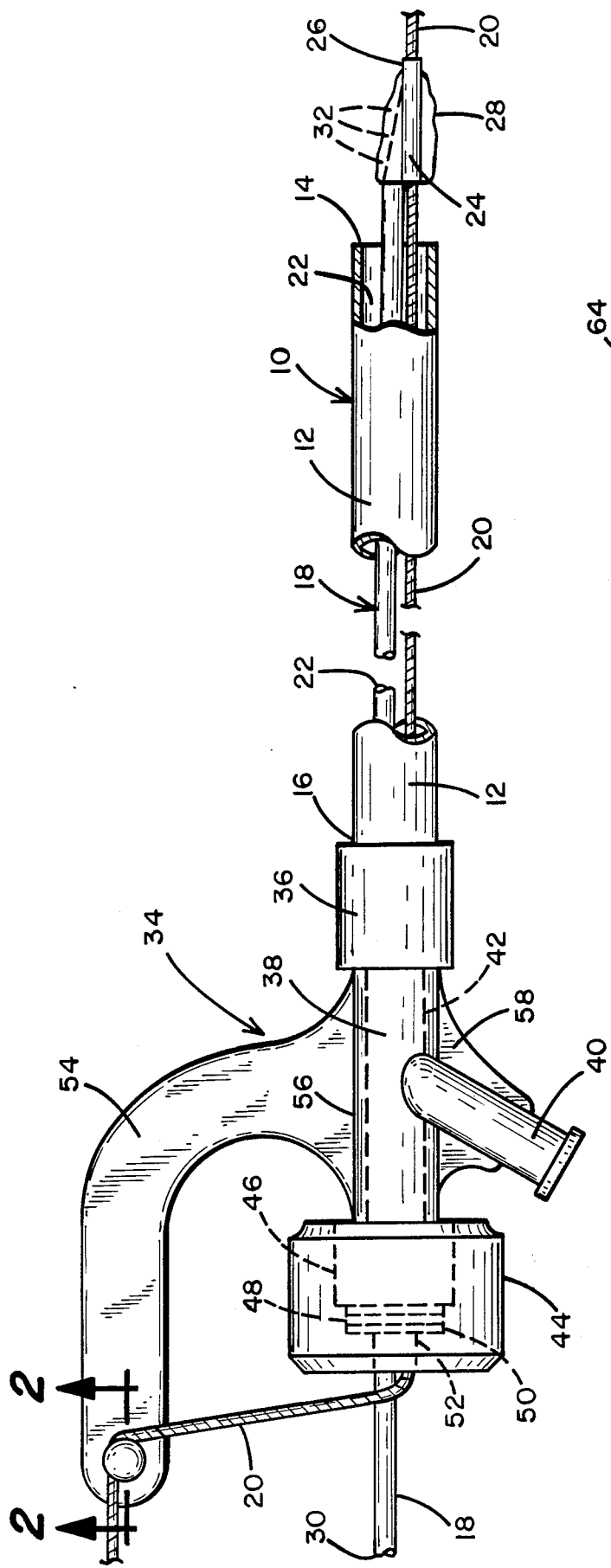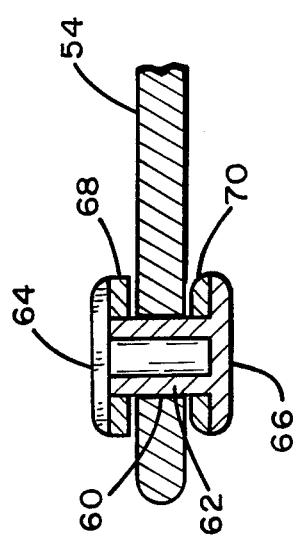

CATHETER Y-CONNECTOR WITH GUIDEWIRE LOCKING MEANS

BACKGROUND OF THE INVENTION

I. Field of the Invention

This invention relates generally to apparatus for performing transluminal angioplasty and related procedures, and more particularly to an improved Y-connector or hub for attachment to the proximal end of a guide catheter for limiting movement of a guidewire used in the placement of the working catheter within the vascular system.

II. Discussion of the Prior Art

In carrying out various surgical procedures, such as coronary artery balloon angioplasty, a balloon-tipped catheter must be routed through the vascular system and across the stenotic lesion so that when the balloon tip on the working catheter is inflated, the partially occluded coronary artery will be spread to a patent condition. In carrying out this procedure, an incision is usually made in the patient's leg to gain access to the femoral artery and a relatively large diameter guiding catheter is inserted through an introducer and routed through the vascular system until its distal end approaches the coronary ostium.

Following the insertion of the guide catheter, a relatively small diameter flexible guidewire is inserted through the proximal end of the guide catheter and advanced through it until the distal end of the guidewire exits the distal end of the guide catheter. By appropriately manipulating the proximal end portion of the guidewire, the physician is able to steer the guidewire into the coronary artery to be treated. Once the guidewire has been advanced so that its distal end is downstream of the lesion to be treated, a balloon catheter, such as described in U.S. patent application Ser. No. 893,558, filed July 14, 1986, and entitled DILATION CATHETER is fitted over the guidewire in the manner described in that application and then fed through the guide catheter. In that the distal end portion of the balloon-tipped catheter is captured onto the guidewire, as the balloon catheter exits the guide catheter, it follows the guidewire until the balloon is made to bridge the stenotic lesion to be treated.

The angioplasty procedure often dictates that working catheters having balloons of differing shapes and diameters be utilized successively. Thus, it is frequently required that a first balloon catheter be removed and replaced sequentially with one or more other working catheters. It is important that the guidewire remain in place until the procedure is completed, thus avoiding the necessity of repositioning the guidewire. When it is considered that several different working catheters are passed back and forth along the guidewire during the course of a procedure, it has required that the physician or a nursing attendant be able to readily grasp and hold the proximal ends of both the guidewire and guide catheter as the working catheters are repositioned. This is an impediment to the physician's ability to effectively manipulate the working catheter in that both hands are occupied with holding the guidewire and guide catheter.

All of the foregoing is by way of background for a better understanding of the construction and use of the present invention. In accordance with the present invention, the conventional Y-connector or hub used on the distal end of the guide catheter is replaced by a hub having an arm extending laterally and proximally from an exterior side surface thereof. This arm extends slightly beyond the proximal end of the hub body and on the free end of the arm is a releasable clamp which may be used to grip the guidewire and thereby hold it fixed relative to the guide catheter. Because of this clamping arrangement, there is no relative movement of the guidewire within the guide catheter and, hence, the possibility that the guidewire is inadvertently retracted is greatly reduced. Moreover, the lateral displacement of the proximal ends of the guidewire and working catheter provided by the arm maintains the guidewire out of the way when manipulating the working catheter.

OBJECTS

It is accordingly a principal object of the present invention to provide an improved Y-connector or hub for a vascular guide catheter.

Another object of the invention is to provide a guide catheter having a proximal hub including means for clamping a guidewire thereto.

Yet another object of the invention is to provide an improved catheter assembly for use in coronary angiography or angioplasty procedures, including a guide catheter, a guidewire insertable therethrough and a working catheter movable about said guide wire where the guide catheter has a proximal hub which includes means for immobilizing the guidewire relative to the guide catheter and spacing the guidewire's proximal end relative to that of the working catheter.

SUMMARY OF THE INVENTION

The foregoing characteristics, advantages and objects of the present invention are realized by providing as a part of the proximal hub on a guide catheter, a laterally and proximally extending arm where the arm includes a means for frictionally engaging and clamping a portion of a guidewire extending outwardly beyond the proximal end of the guide catheter's hub.

DESCRIPTION OF THE DRAWINGS

FIG. 1 is an enlarged, partially sectioned view illustrating a guide catheter having a hub incorporating the present invention; and FIG. 2 is a cross-sectional view taken along the lines 2—2 in FIG. 1.

DESCRIPTION OF THE PREFERRED EMBODIMENT

Referring to FIG. 1, there is illustrated a guide catheter, indicated generally by numeral 10, which comprises an elongated, flexible plastic tube 12 having a distal end 14 and a proximal end 16. Typically, the guide catheter body 12 may be approximately one meter in length and may have an outside diameter in the range of from 2.34 mm to 3.05 mm and an inside diameter of approximately 1.90 mm.

In the view of FIG. 1, the guide catheter is seen to contain a working catheter 18 and a guidewire 20 running in side-by-side relationship through the lumen 22 of the guide catheter. The working catheter may be used for diagnostic purposes or, as illustrated in FIG. 1, may be a balloon angioplasty catheter. The working catheter 18 and the guidewire 20 are preferably of the type described in the aforereferenced application Ser. No. 893,558 and, as such, the guidewire 20 does not extend through the main lumen 22 of the working catheter along its entire length but, instead, passes through a short length of tubing 24 located near the distal end 26 of the working catheter and beneath the expander (balloon) 28. The expander member 28 may be inflated and deflated by injecting or aspirating a fluid at the proximal end 30 of the working catheter. The fluid traverses the lumen 22 and passes through ports 32 formed through the distal end portion of the tube beneath the expander member 28.

Attached to the proximal end of the tubular guide catheter body 12 is a hub member identified generally by numeral 34. The hub is illustrated as being a so-called Y-connector which, except for the feature yet to be described, is conventional in its construction. That is to say, it includes a conventional luer swivel 36 which allows the hub 34 to rotate relative to the guide catheter body 12 to which it is attached. Included in the swivel are suitable O-ring seals to preclude blood from seeping through the swivel joint when the assembly shown is being used in a surgical procedure. The hub 34 also includes a tubular body member 38 having a luer fitting 40 extending at a predetermined angle to the longitudinal axis of the body 38, thus accounting for the common designation, "Y-connector". The luer fitting 40 communicates with the longitudinal bore 42 extending through the body 38 and provides a means whereby a suitable X-ray contrast medium may be injected into the lumen 22 of the guide catheter for allowing fluoroscopic observation as the guide catheter is being routed through the vascular system. Moreover, the port in the tube 40 may be available for taking pressure measurements.

Affixed to the proximal end of the hub body 38 is a compression cap 44 which is received on a cylindrical enlargement 46 integrally formed with the tubular body 38. One or more elastomeric gaskets 48 fit into a recess 50 formed in the end cap 44. The proximal end portions of the guidewire 20 and the working catheter 18 pass through a bore 52 formed in the end cap 44 as illustrated. When the compression cap 44 is twisted onto the enlargement 46, the gaskets 48 are compressed to effectively seal the exit port 52 to prevent loss of blood or other fluids through that port.

In accordance with the present invention, the hub 34 is also provided with a laterally and proximally extending arm 54 which is preferably integrally molded to the hub's tubular body 38. Alternatively, it may be separately bonded to the exterior surface of the tube 38 along the line 56. While not essential, it has been found convenient to form the arm 54 so as to be coplanar with the support web 58 joining the tubular branch 40 to the body member 38. As noted in the drawing of FIG. 1, the arm 54 extends proximally beyond the end of the compression cap 44.

With reference to FIGS. 1 and 2, it can be seen that the arm 54 includes an aperture 60 extending through the thickness dimension thereof and fitted through this aperture is a shaft 62 whose length is greater than the thickness dimension of the arm 54. The shaft 62 has a predetermined clearance fit with the aperture 60 and formed on opposed ends of the tube 62 are end cap members 64 and 66. Elastomeric washers 68 and 70 are adhesively bonded to the end caps 64 and 66 as can be readily observed in FIG. 2.

OPERATION

When the apparatus of the present invention is employed in, for example, a balloon angioplasty procedure, the first step in the procedure is to insert the guide catheter into an incision made in the femoral artery and then advance the guide catheter through the vascular system until the distal end 14 of the guide catheter approaches the coronary ostium of the heart. This procedure is facilitated when a suitable radiopaque die is introduced, via side port 40, of the Y-connector 34 during the guide catheter placement step.

Next, an elongated guidewire 20 is fed through the entrance port 52 formed in the compression cap 44 and is fed through the tubular body 38 of the hub 34 and through the lumen 22 of the guide catheter until the guidewire is steered into the coronary artery to be treated with its distal tip beyond the stenotic lesion.

Next, the working catheter 18 has its distal tube portion 24 fitted over the proximal end of the guidewire 20 and then it is pushed through the port 52 and the sealing gaskets 48. Once the distal end portion 26 of the working catheter has been moved into the catheter body 38, the physician may then wrap the guidewire 20 over the shaft 62 and between the side surface of the arm 54 and the end cap 64. Now, when a lateral force is applied to the end cap 64, the guidewire 20 is effectively captured between the elastomeric surface 68 and the side surface of the arm 54. Frictional forces between the shaft 62 and the aperture 60 hold the clamp closed.

Once the guidewire 20 is so clamped, its proximal end is held out of the way and the working catheter 18 may more readily continue to be fed through the guide catheter 10 with the guidewire serving as a rail along which the working catheter 18 is steered. Once the expander member 28 is appropriately positioned relative to the stenotic lesion, an inflation fluid may be injected into the lumen of the working catheter at its distal end and this fluid will flow the length of the catheter and through the ports 32 to inflate the expander 28. Inflation of the balloon 28 serves to spread the occluded opening in the coronary artery being treated.

In the course of an angioplasty procedure, it often becomes necessary to start with a balloon of a relatively small outer diameter and then successively substitute working catheters having expander members of increasingly larger diameter. Because of the provision of the arm 54 on the hub member 34 with its guidewire clamping arrangement illustrated in FIG. 2, it is no longer required that the surgeon or the surgical attendant hold onto the proximal end portion 20 of the guidewire as he or she either advances or retracts the working catheter. It is only required that the guidewire 20 be unlocked when a working catheter is to be totally removed from the guidewire or when a new working catheter is to be fed onto that guidewire.

When the guidewire is in the desired, proper position across the stenosis, any movement of the guidewire while advancing or retracting the working catheter, is generally detrimental. The arm and locking means which is added to the Y-connector is used to fix the guidewire in relationship to the guiding catheter. This permits the balloon catheter to be advanced and withdrawn without any inadvertent dislocation of the guidewire in the stenosis. A further advantage of the present invention is that the arm and lock arrangement maintains the guidewire and working catheter separated, facilitating the grasping of one or the other individually by a surgeon wearing surgical gloves, which gloves may be moist and somewhat slippery from exposure to body fluids.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself. For example, various devices for clamping the guidewire may be devised as a replacement for the push-button clamp disclosed herein. Hence, the scope of the invention should be determined from the following claims.

What is claimed is:

1. A guide catheter for use in cardiovascular diagnostic or surgical procedures comprising:
    (a) an elongated, flexible, non-bifurcated tube having a distal end and a proximal end, said tube having an internal lumen of a diameter sufficiently large to receive a working catheter and a guidewire therein in a loose-fitting, side-by-side disposition, said guidewire and said working catheter being of a greater length than said tube such that portions of said guidewire and said working catheter can be made to extend beyond both said distal end and said proximal end of said guide catheter; and
    (b) hub means having a single entry/exit port and affixed to said proximal end of said guide catheter for maintaining the portions of said guidewire and said working catheter extending through said entry/exit port of said hub means spaced apart from one another for ease of gripping and with said guidewire being selectively clamped against movement relative to said guide catheter.

2. A guide catheter for use in cardiovascular diagnostic or surgical procedures comprising:
    (a) an elongated, flexible, non-bifurcated tube having a distal end and a proximal end, said tube having an external lumen of diameter sufficiently large to receive a working catheter and a guidewire therein in a loosely-fitting, side-by-side disposition;
    (b) a hub member secured to said proximal end of said tube, said hub member including a tubular body having a distal end and a proximal end with a single entry/exit port through said proximal end of said hub member and an arm of a predetermined thickness dimension extending laterally and proximally from an exterior surface of said tubular body; and
    (c) releasable clamping means affixed to said arm for receiving said guidewire.

3. The guide catheter as in claim 2 wherein said tubular body and said arm are integrally molded from plastic.

4. The guide catheter as in claim 2 wherein said arm includes an aperture through said thickness dimension thereof.

5. The guide catheter as in claim 4 wherein said clamping means fits through said aperture.

6. The guide catheter as in claim 4 wherein said clamping means includes a central shaft of a length greater than the thickness dimension of said arm and reciprocally movable through said aperture with a predetermined clearance fit, said shaft including end caps on opposed ends thereof.

7. The guide catheter as in claim 6 and further including elastomeric washers surrounding said shaft and bonded to said end caps.

8. The guide catheter as in claim 2 wherein said hub member is rotatably secured to said proximal end of said tube.

9. The guide catheter as in claim 2 and further including a compression cap fitted onto said proximal end of said tubular body, said compression cap having a bore therethrough for allowing said guidewire and working catheter to pass therethrough while blocking the outflow of body fluids.

* * * * *

UNITED STATES PATENT AND TRADEMARK OFFICE
CERTIFICATE OF CORRECTION

PATENT NO. : 4,844,092

DATED : July 4, 1989

INVENTOR(S) : Mark A. Rydell and Richard L. Goodin

It is certified that error appears in the above-identified patent and that said Letters Patent is hereby corrected as shown below:

Column 6, line 1, "external" should read -- internal --.

Column 6, line 1, before "diameter" insert -- a --.

Signed and Sealed this

Eighth Day of May, 1990

Attest:

HARRY F. MANBECK, JR.

*Attesting Officer*      *Commissioner of Patents and Trademarks*